(12) United States Patent
Niederauer et al.

(10) Patent No.: US 10,327,703 B2
(45) Date of Patent: Jun. 25, 2019

(54) VITAL SIGN MONITORING DEVICE

(71) Applicant: WACIAN LLC, Salt Lake City, UT (US)

(72) Inventors: Stefan Julius Niederauer, Salt Lake City, UT (US); Azmi Alaaeldin Ahmad, Salt Lake City, UT (US); Benjamin Reed Fogg, Salt Lake City, UT (US)

(73) Assignee: WACIAN, LLC, Salt Lake City, UT (US)

( * ) Notice: Subject to any disclaimer, the term of this patent is extended or adjusted under 35 U.S.C. 154(b) by 232 days.

(21) Appl. No.: 15/478,917

(22) Filed: Apr. 4, 2017

(65) Prior Publication Data

US 2017/0281088 A1     Oct. 5, 2017

Related U.S. Application Data

(60) Provisional application No. 62/317,969, filed on Apr. 4, 2016.

(51) Int. Cl.
*A61B 5/00* (2006.01)
*A61B 5/1455* (2006.01)
*A61B 5/01* (2006.01)

(52) U.S. Cl.
CPC .............. *A61B 5/6833* (2013.01); *A61B 5/01* (2013.01); *A61B 5/14552* (2013.01); *A61B 2560/0412* (2013.01); *A61B 2560/0443* (2013.01); *A61B 2562/227* (2013.01)

(58) Field of Classification Search
CPC ... A61B 5/6833; A61B 5/01; A61B 2562/227; A61B 2560/0412; A61B 2560/0443; A61B 5/14552
See application file for complete search history.

(56) References Cited

U.S. PATENT DOCUMENTS

| | | | |
|---|---|---|---|
| 2008/0275327 A1* | 11/2008 | Faarbaek | A61B 5/0002 600/382 |
| 2011/0051982 A1* | 3/2011 | Abreu | G02C 3/003 381/384 |
| 2014/0121557 A1* | 5/2014 | Gannon | A61B 5/002 600/549 |
| 2016/0149292 A1* | 5/2016 | Ganton | A61B 5/01 600/300 |

* cited by examiner

*Primary Examiner* — Christine H Matthews
*Assistant Examiner* — Joshua Daryl D Lannu
(74) *Attorney, Agent, or Firm* — Workman Nydegger

(57) ABSTRACT

The present disclosure describes a vital sign monitoring device configured for monitoring one or more patient vital signs. The device includes a disposable patch assembly attachable to a reusable electronics package. The patch assembly includes an adhesive layer for adhering to a patient's skin. A vital sign sensor is embedded within the adhesive layer. A flexible circuit connects to the sensor on an upper side of the adhesive layer, and provides electrical contact between the sensor and the electronics package. The electronics package includes a battery and microcontroller for powering and controlling the sensor.

20 Claims, 11 Drawing Sheets

VITAL SIGN MONITORING DEVICE

CROSS-REFERENCE TO RELATED APPLICATIONS

This application claims priority to and the benefit of U.S. Provisional Patent Application Ser. No. 62/317,969, filed on Apr. 4, 2016 and titled "VITAL SIGN MONITOR," the disclosure of which is incorporated herein by this reference in its entirety.

BACKGROUND

The monitoring of a patient's vital signs is one of the most fundamental aspects of proper patient care. Vital signs such as body temperature, heart rate, respiration rate, and blood pressure are routinely determined and monitored by health care providers. In a hospital or other emergency care setting, vital sign monitoring is typically done on a continual basis, at least in relatively more developed regions of the world. When one or more vital signs begin to degrade, the speed at which attending health care providers are able to be notified and react can be the difference between life and death of the patient.

Typically, vital sign monitors are constructed as bedside devices attached to hospital beds or carts, or are integrally built into the walls of a facility room. Usually, these devices are powered through standard wall outlets (mains electricity). The utility of such devices is substantially reduced in areas where mains electricity is unavailable, insufficient, or unreliable, such as in developing nations, in certain emergency situations, in remote locations, and in war zones, for example. Further, the typically large and clunky construction of such devices limits their usefulness in circumstances where space is a concern. Additionally, conventional vital sign monitors are relatively costly, making them difficult to obtain and use in many situations where they could otherwise benefit patient care and improve outcomes.

BRIEF SUMMARY

The present disclosure describes embodiments of a vital sign monitoring device configured as a compact and readily usable tool for patient care. Certain embodiments described herein are operable without stable power sources, beneficially enabling vital sign monitoring in circumstances where such power is unavailable or unreliable. Certain embodiments described herein have a relatively compact construction, making storage and/or stockpiling of such devices easier and allowing such devices to be readily available when needed. Certain embodiments described herein are efficiently and economically constructed, such devices thereby being providable at relatively low cost.

At least some of the embodiments described herein may be effectively utilized in circumstances where conventional vital sign monitoring devices are unavailable, such as in developing regions, remote locations, emergency situations, war zones, and the like. Certain embodiments described herein can therefore expand the circumstances in which vital signs can be effectively monitored.

An embodiment of a vital sign monitoring device includes a patch assembly and an attachable electronics package. In some embodiments, the patch assembly is single-use and/or disposable whereas the electronics package may be detached and reused with other unused patch assemblies.

In some embodiments, a patch assembly includes an adhesive layer configured for application and adherence to a patient's skin. The adhesive layer may be hydrogel based, for example. One or more vital sign sensors, such as a pulse oximetry sensor and/or temperature sensor, are embedded within the adhesive layer. A circuit member, which is preferably formed as a flexible circuit member, is disposed on an upper side of the adhesive layer (i.e., the side opposite the side adhering to the patient) and is electrically coupled to the one or more embedded sensors. An inlay with a raised perimeter section surrounds the circuit member and defines an interior space for receiving components of an electronics package when the electronics package is coupled to the patch assembly.

The electronics package includes a fastener element to engage with and attach to the inlay of the patch assembly. The electronics package also includes a power supply and a microcontroller. When the electronics package is coupled to the patch assembly, the circuit member is brought into electrical contact with the microcontroller and the power supply, enabling the powering of the one or more sensors and enabling sensor readings to be transmitted from the one or more sensors to the microcontroller.

Certain embodiments include a single-use attachment mechanism configured to limit operability of the patch assembly after an initial attachment and detachment. Promoting single-use of patch assemblies encourages more sanitary use of the device and can reduce disease transmission. In some embodiments, the initial attachment of the electronics package to the patch assembly causes the circuit member to be bent or crimped. When the electronics package is subsequently detached, the crimped circuit member moves out of alignment with a corresponding electrical contact of the electronics package. Subsequent attempts to attach the electronics package to the patch assembly will not result in a proper electrical connection between the separate pieces.

In some embodiments, the raised perimeter section of the inlay includes a hinge assembly configured to engage with the electronics package when the electronics package is initially attached. As the electronics package engages with the inlay, the hinge assembly rotates from a receiving configuration to a blocking configuration. Once the hinge assembly has been moved to the blocking configuration, subsequent attachment attempts will be made more difficult.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which.

DETAILED DESCRIPTION

Figure 1:
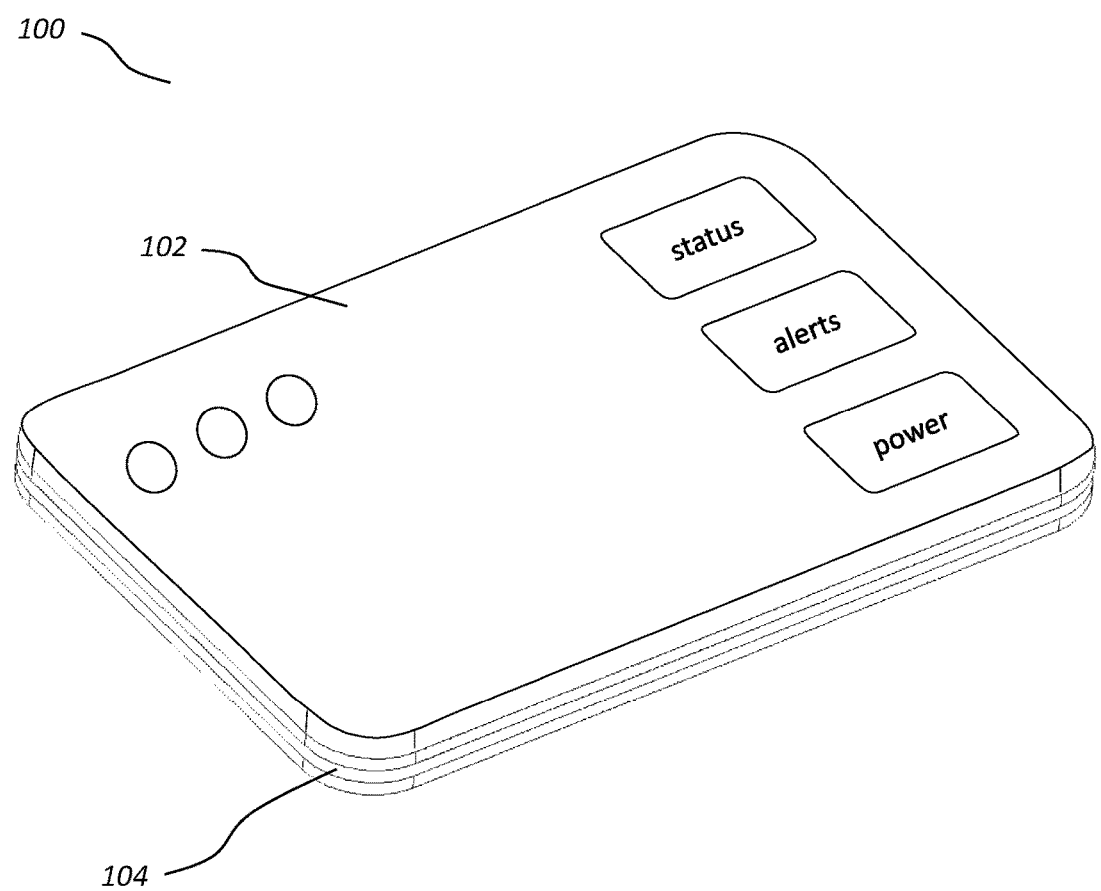
FIG. 1 illustrates an exemplary vital sign monitoring device.

FIG. 1 illustrates an exemplary vital sign monitoring device 100 which may be positioned on a patient's skin to effectively monitor the patient's vital signs. The illustrated monitoring device 100 includes an electronics package 102 coupled to a patch assembly 104. The patch assembly 104 is configured to contact and adhere to the patient's skin, and the electronics package 102 is configured to couple to the upper side of the patch assembly 104. As explained in more detail below, the patch assembly 104 includes one or more embedded sensors for which are brought into an operative spatial relationship with the patient's skin when the monitoring device 100 is positioned on a patient. The electronics package 102 may function to power the sensor(s), receive readings from the sensor(s), and/or send readings to one or more communicatively coupled computer devices.

In contrast to conventional vital sign monitoring devices, the illustrated monitoring device 100 is relatively compact. For example, the monitoring device 100 may have a width of about 2.5 to 5 cm, a length of about 2.5 to 5 cm, and a height or thickness of about 0.5 to 1.5 cm (with size constraints being a function mostly of power requirements and battery size). Monitoring devices having dimensions within those ranges have shown to be capable of holding necessary functional components while also providing effective adherence to the patient. In particular, the length and width of the monitoring device 100 provide sufficient surface area for adhesion to the patient, without causing over-adhesion, skin tightening, and associated skin irritation and patient discomfort. Monitoring devices of even smaller dimensions may also be utilized as battery power requirement technology improves.

Figure 2:
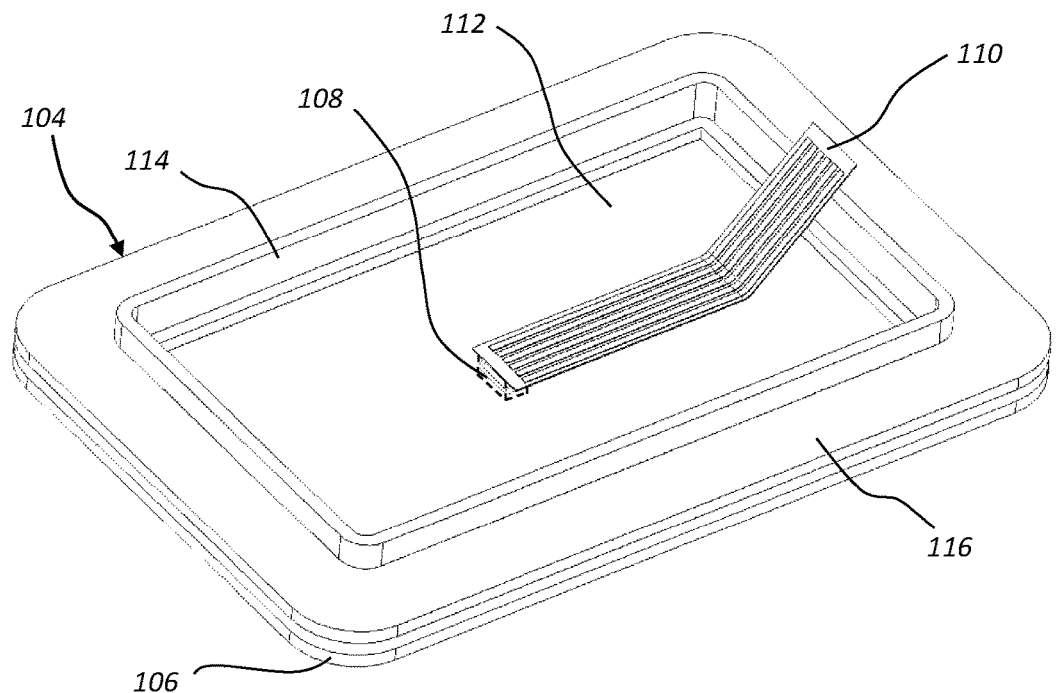
FIGS. 2 through 4 illustrate various views of a patch assembly of the vital sign monitoring device of FIG. 1.
Figure 3:
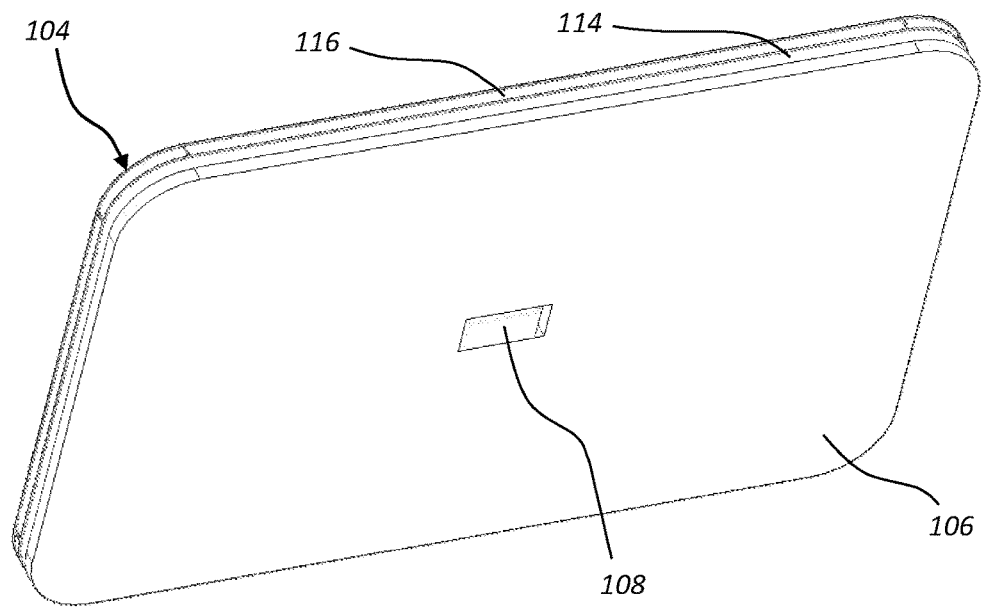
Figure 4:
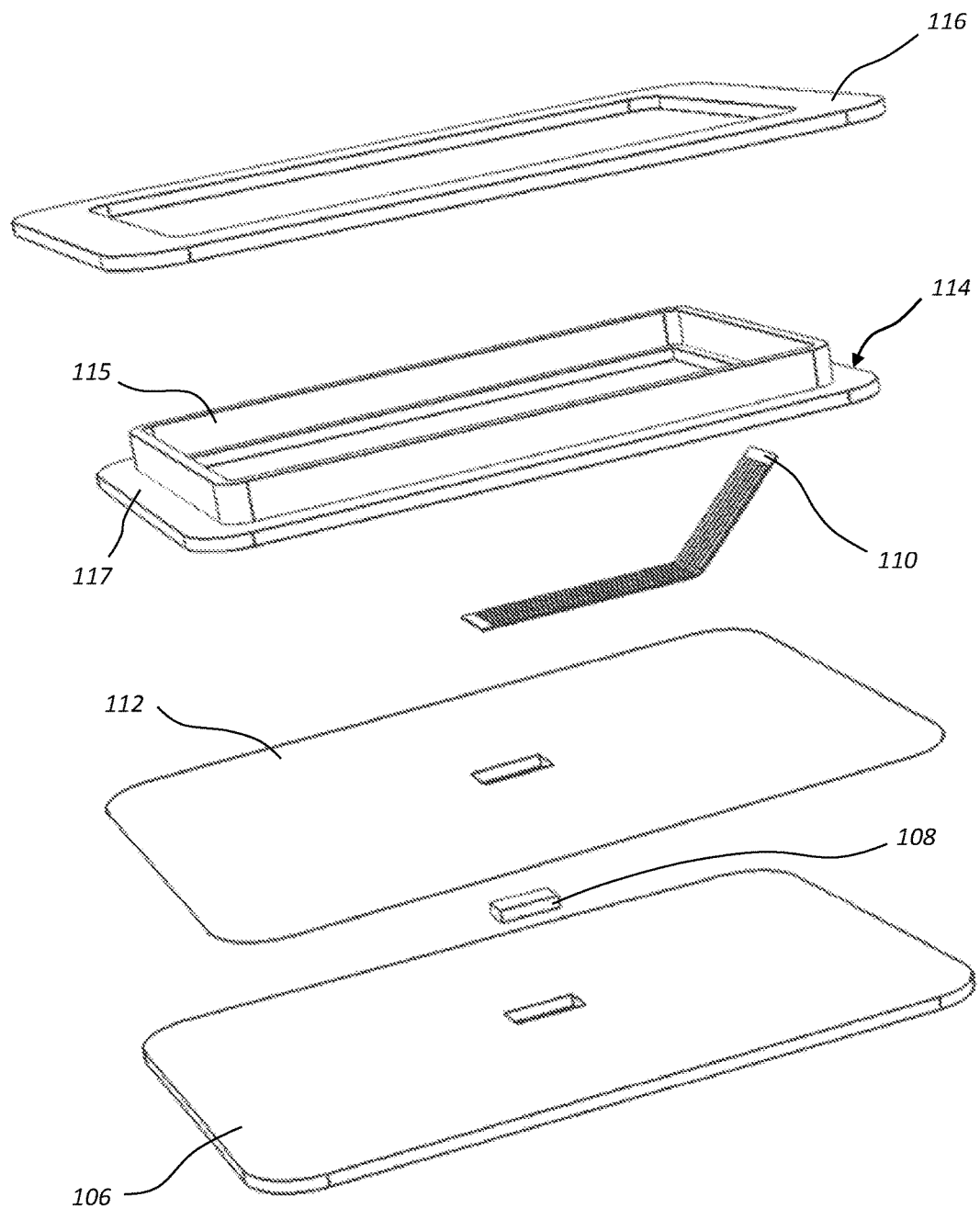

FIGS. 2 through 4 illustrate various views of the patch assembly 104. FIG. 2 shows the upper side (i.e., the side farthest from the patient's skin when the device is positioned on the patient) of the patch assembly 104. The overlying electronics package 102 of FIG. 1 has been removed to better show some of the interior components of the patch assembly 104. FIG. 3 shows lower side (i.e., the side closest to the patient's skin when the device is positioned on the patient) of the patch assembly 104. FIG. 4 is an exploded view showing different layers of the illustrated embodiment.

In the illustrated embodiment, the lowermost layer is an adhesive layer 106. The adhesive layer 106 is configured to contact and adhere to the patient's skin when the device is positioned on a patient. The adhesive layer 106 may be formed from any suitable, medical-grade adhesive composition. In preferred embodiments, the adhesive layer 106 includes a medical-grade hydrogel component. Some embodiments may additionally or alternatively include one or more polymers of polyvinylpyrrolidone, ethyl cellulose, pyroxylin/nitrocellulose, poly(methylacrylate-isobutene-monoisopropylmaleate), acrylate, or siloxane, for example.

As shown, the adhesive layer 106 includes an aperture to allow passage of a sensor 108 through the adhesive layer 106 where it can contact the patient's skin. Preferably, the sensor 108 is disposed so as to be flush with the lower side of the adhesive layer 106. Although one sensor 108 is shown in the illustrated embodiment, other embodiments may include a plurality of sensors, and although a single sensor 108 is illustrated throughout much of the description, it will be understood that the same principles as described may be applied to multi-sensor embodiments.

The monitoring device 100 may include, for example, a pulse oximetry sensor (e.g., a reflectance pulse oximetry sensor), a temperature sensor (e.g., a thermistor, thermocouple, etc.), and/or any other suitable monitoring sensor capable of being embedded within the monitoring device 100. Based on the included one or more sensors, the monitoring device 100 may be configured to monitor one or more of heart rate, respiration rate, oxygen saturation, body temperature, blood pressure (e.g., through an indirect calculation based on other primary readings), and blood carbon dioxide, for example.

The adhesive layer 106 preferably has a thickness that accommodates the sensor 108 and also allows the sensor 108 to extend to the lower side for contacting the patient's skin. The adhesive layer 106 may have a thickness, for example, of about 0.2 mm to about 1.2 mm, or about 0.4 mm to about 0.8 mm, or about 0.6 mm. Adhesive layers with thicknesses within these ranges have shown to effectively support and position corresponding sensors while also providing sufficient structure for adherence to the patient.

As shown, the sensor 108 extends upwards through the adhesive layer 106 to contact a circuit member 110. In preferred embodiments, the circuit member 110 is a flexible circuit (e.g., formed via chemical etching of a copper-coated polymer film). In other embodiments, a rigid circuit structure may be utilized. As explained in more detail below, the circuit member 110 provides electrical connection between the sensor 108 and the electronics package 102 when the electronics package 102 is coupled to the patch assembly 104.

As best shown in the exploded view of FIG. 4, the patch assembly 104 may also include a barrier layer 112 disposed between the circuit member 110 and the adhesive layer 106. The barrier layer 112 is formed from an electrically insulative material (e.g., a suitable polymer), and functions to reduce electrical interference passing from the adhesive layer 106 to the circuit member 110. As shown, the barrier layer 112 includes an aperture that coincides with the aperture of the adhesive layer 106 to allow passage of the sensor 108 upwards to the circuit member 110. The barrier layer 112 may be relatively thin, such as about 0.2 mm or less.

The illustrated embodiment includes an inlay 114 disposed above the adhesive layer 106 (and barrier layer 108 when included). The inlay 114 is configured as a frame having a raised perimeter section 115 and a substantially horizontal outer perimeter section 117 (best shown in FIG. 4). The raised perimeter section 115 defines a window through which the circuit member 110 may connect with corresponding connecting elements of the electronics package 102. The inlay 114 creates sufficient interior space within the patch assembly 104 to receive components of the electronics package 102 when the electronics package 102 is attached. The height of the inlay 114 therefore need only be sufficient to receive the corresponding components of the electronics package 102. In present embodiments, for example, the inlay 114 may have a height of about 3 to 6 mm.

An overlay 116 may be positioned over the inlay 114 to seal/enclose the underlying layers and/or to provide additional structure to the patch assembly 104. In the illustrated embodiment, the overlay 116 is sized to fit around the raised perimeter section 115 and to sit upon the outer perimeter section 117. As with the inlay 114, the overlay 116 defines a window through which the circuit member 110 and corresponding components of the electronics package 102 can connect.

The inlay 114 may be formed from any suitable material capable of providing sufficient structural support to the device. The inlay 114 may be formed from a polymer, metal, or alloy material, for example. The overlay 116 may be formed from a polymer, fabric, or other suitable material capable of sealing/connecting the other components of the patch assembly 104 together.

Figure 5:
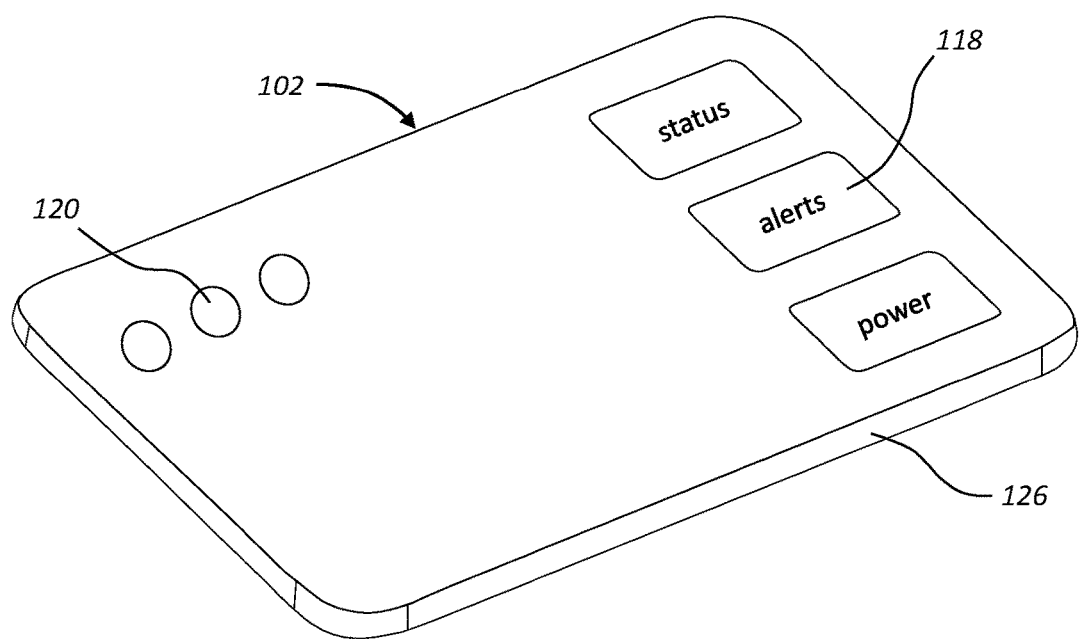
FIGS. 5 and 6 illustrate an electronics package of the vital sign monitoring device of FIG. 1.
Figure 6:
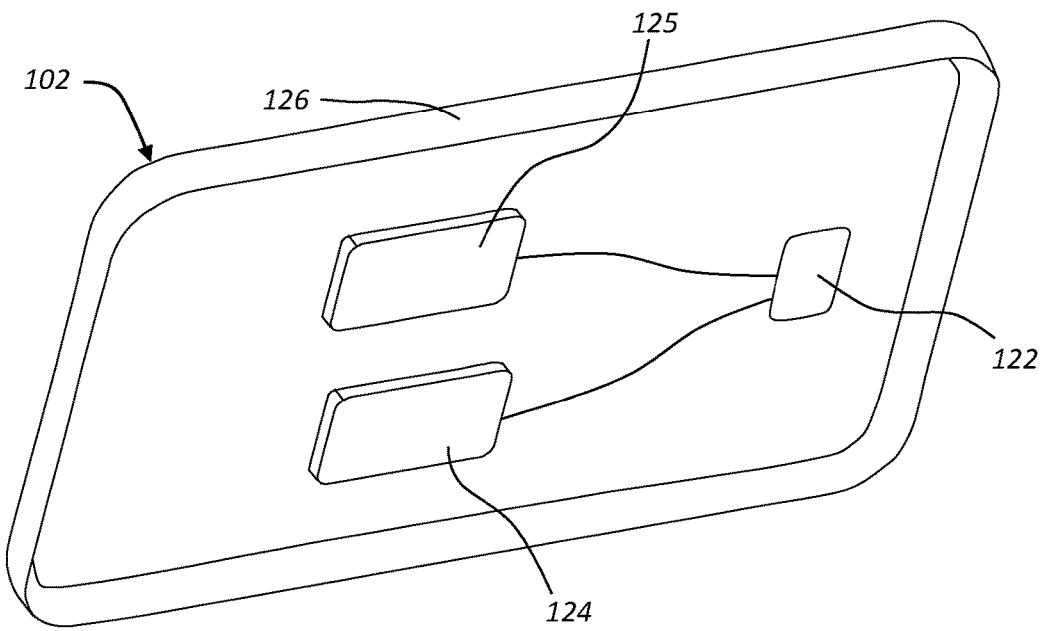

FIGS. 5 and 6 illustrate the exemplary electronics package 102. FIG. 5 shows the upper side of the electronics package 102, and FIG. 6 shows the underside and interior. As shown in FIG. 5, the casing of the electronics package 102 may include one or more indicators 118 and/or one or more controls 120. The indicators 118 may include, for example, one or more lights, displays, audio speakers, or combinations thereof. Display readings may relate to device status, power levels, alerts or alert history, current readings, or combinations thereof. The one or more controls 120 may be buttons, knobs, switches, or other selectively manipulatable element providing control over functionality of the device (e.g., on/off switching, monitoring parameters, measurement sample rate, measurement type(s), output type(s), etc.).

FIG. 6 illustrates the underside and interior of the casing of the electronics package 102. The illustrated embodiment includes an electrically conductive contact point 122, a microcontroller system 124, and a power supply 125 (e.g., lithium-ion polymer battery or other suitable battery). When the electronics package 102 is attached to the patch assembly 104, a fastener element, such as rim 126 of the electronics package 102, engages with the raised perimeter section 115 of the inlay 114. In the attached position, the circuit member 110 is brought into contact with the contact point 122, which electrically connects the microcontroller system 124 and power supply 125 to the circuit member 110 and in turn to the sensor 108. The microcontroller system 124 may include several subcomponents which are described in further detail below with respect to FIG. 10.

The casing of the electronics package 102 may be formed from any suitable material providing sufficient structural integrity. In some embodiments, the casing of the electronics package 102 is formed of the same material as the inlay 114 of the patch assembly 104.

The connection between the electronics package 102 and the patch assembly 104 may operate as a friction fit or snap engagement. Other fastening mechanisms (e.g., clamps, screws, magnets) may additionally or alternatively be used. In preferred embodiments, the connection is made according to a mechanism that limits use of the patch assembly 104 to single use. Single use of the patch assembly 104 promotes more sanitary application of the monitoring device 100, and reduces the risks of disease transmission through reuse (accidental or inadvertent) across multiple patients. The electronics package 102, however, is detachable and reusable. In this manner, the monitoring device 100 limits potential unsanitary use while also preserving the typically more expensive components of the device as a reusable portion.

Figure 7:
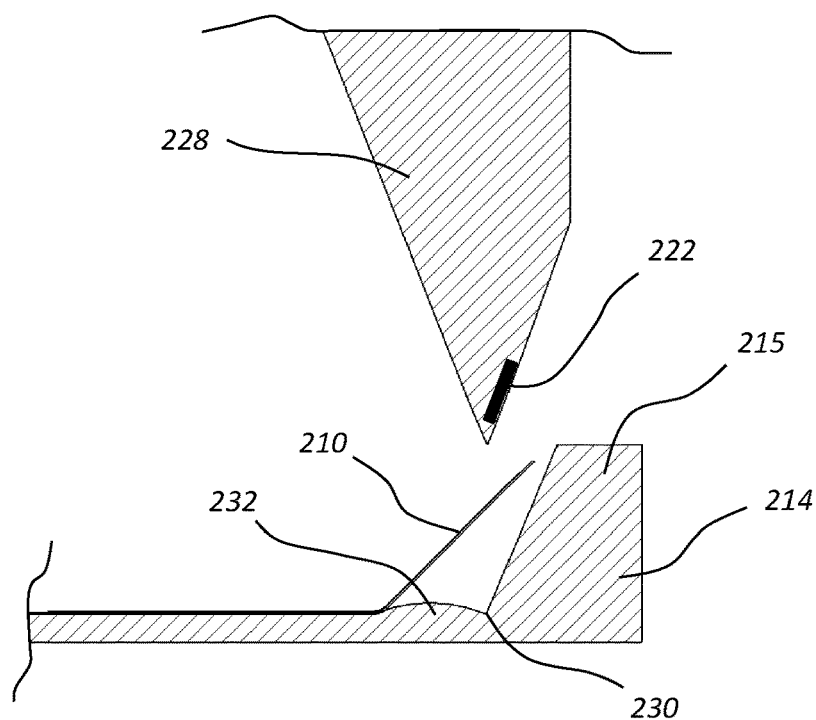
FIGS. 7 through 9 illustrate an embodiment of a single-use connection mechanism for deterring medical misuse of a patch assembly.
Figure 8:
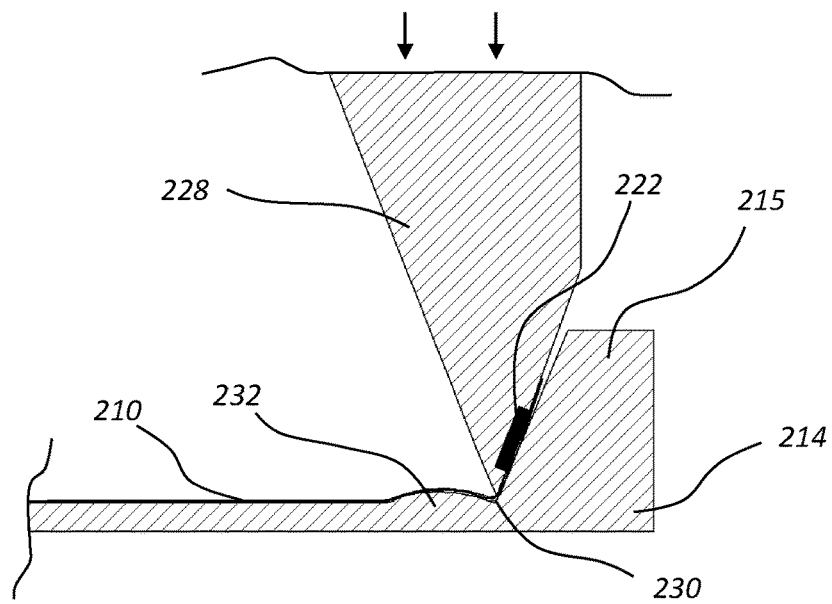
Figure 9:
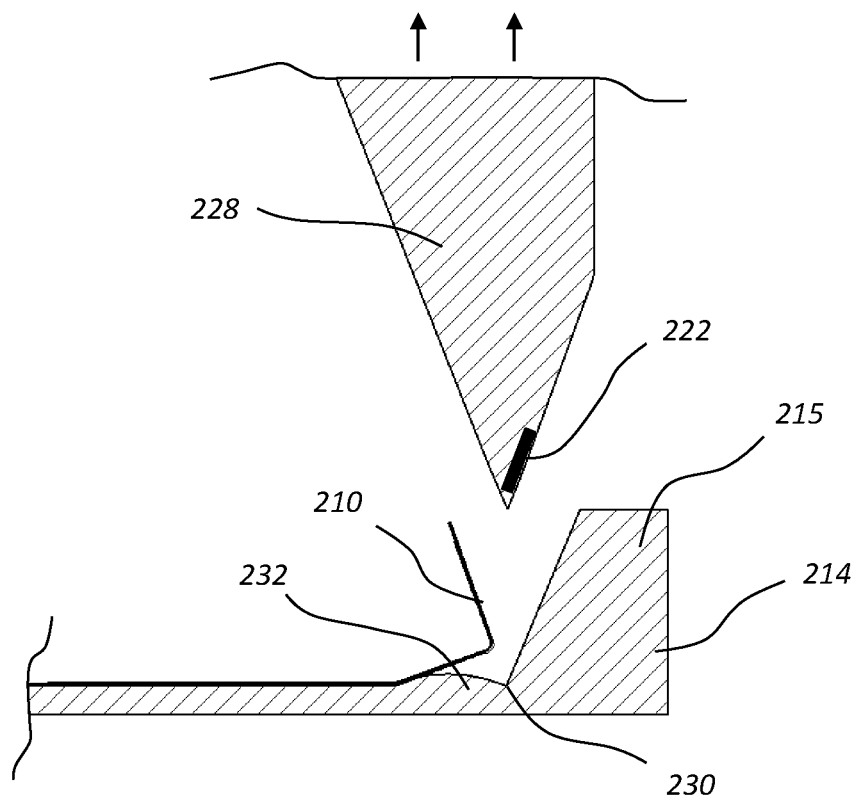

FIGS. 7 through 9 illustrate an example of a single-use mechanism that limits or prevents electrical contact between the patch assembly and electronics package after the initial connection. FIGS. 7 through 9 illustrate a cross-sectional side view of an embodiment showing an inlay 214, a circuit member 210 disposed upon the inlay 214, and a contact point 222 of the electronics package. As shown, the contact point 222 is disposed upon a pointed element 228. The pointed element 228 is shaped to be received into a notch 230 of the inlay 214. As shown, the notch 230 may be disposed between a raised perimeter section 215 of the inlay 214 and a curved surface 232 disposed adjacent to the raised perimeter section 215.

FIG. 7 illustrates the components of the single-use mechanism prior to attachment of the electronics package to the patch assembly. In this position, the free distal end of the circuit member 210 is oriented toward the raised perimeter section 215. FIG. 8 shows the components after the initial attachment of the electronics package to the patch assembly. As shown in FIG. 8, when the electronics package is attached, the contact point 222 is brought into engagement with the circuit member 210, and the pointed element 228 is received into the notch 230. A portion of the circuit member 210 proximal of its free distal end is crimped over the curved surface 232 and into the notch 230.

FIG. 9 illustrates the relative positions of the components upon initial removal of the electronics package. As shown, the pointed element 228 is moved out of the notch 230, severing electrical contact between the circuit member 210 and the contact point 222. As a result of the crimping action of the initial attachment, the circuit member 210 is now bent away from the notch 230. Subsequent attempts to reattach the electronics package will again bring the pointed element 228 into the notch 230, but the induced curvature of the circuit member 210 will not provide the necessary contact between the contact point 222 and the circuit member 210.

Figure 10:
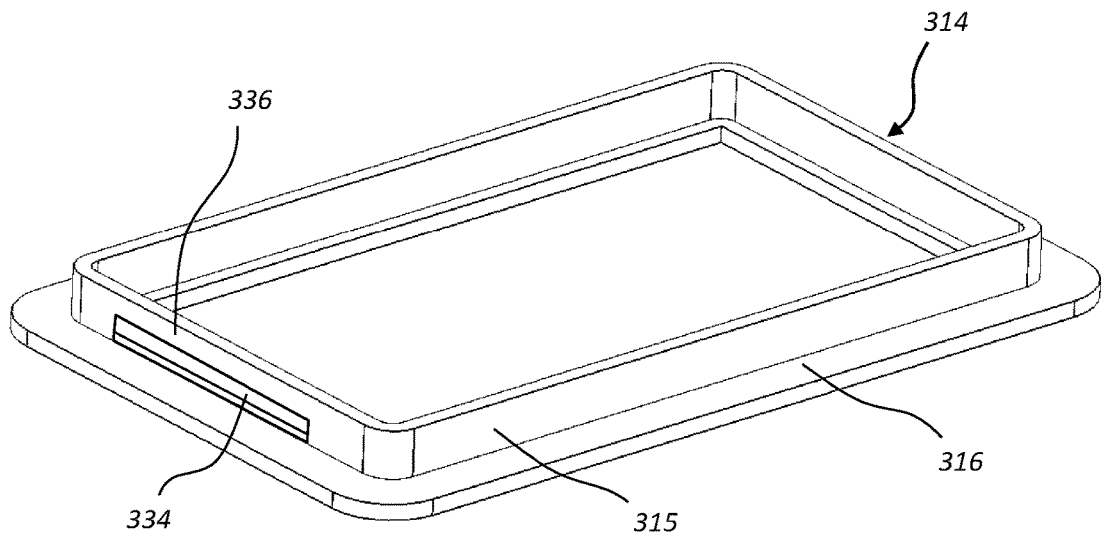
FIGS. 10 through 14 illustrate another embodiment of a single-use connection mechanism for deterring misuse of a patch assembly.

FIGS. 10 through 14 illustrate another embodiment of a single-use mechanism that operates to mechanically prevent reattachment of the electronics package to an already used patch assembly. As shown in FIGS. 10 (isometric view) and 11 (front view), an inlay 314 includes a hinge assembly 334 integrated into at least a portion of the raised perimeter section 315 adjacent to the outer perimeter section 316. The area above the hinge assembly 334 defines an overhang 336.

Figure 11:
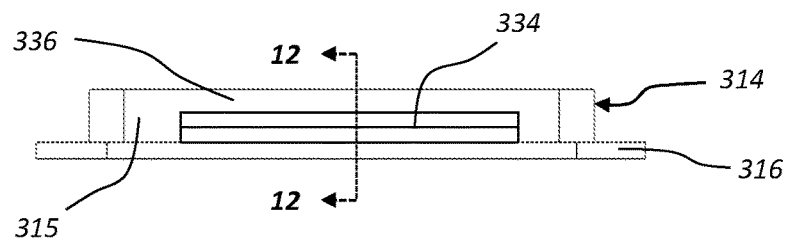
Figure 12:
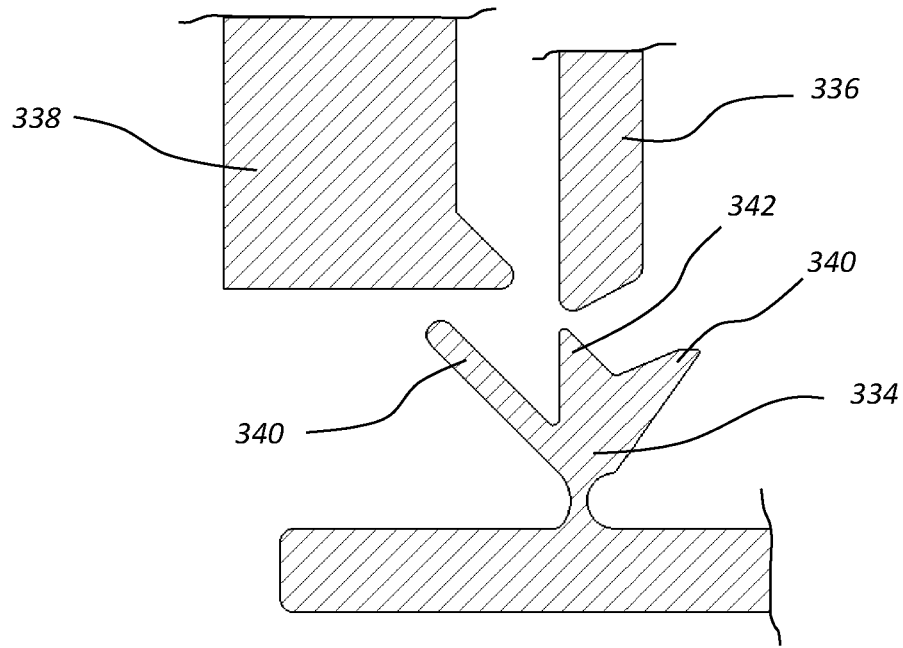
Figure 13:
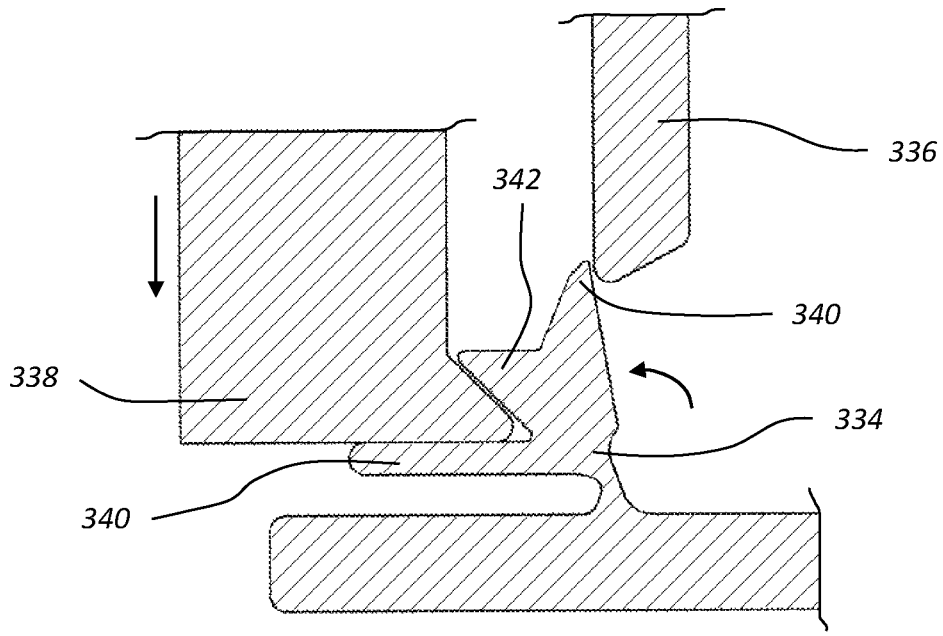
Figure 14:
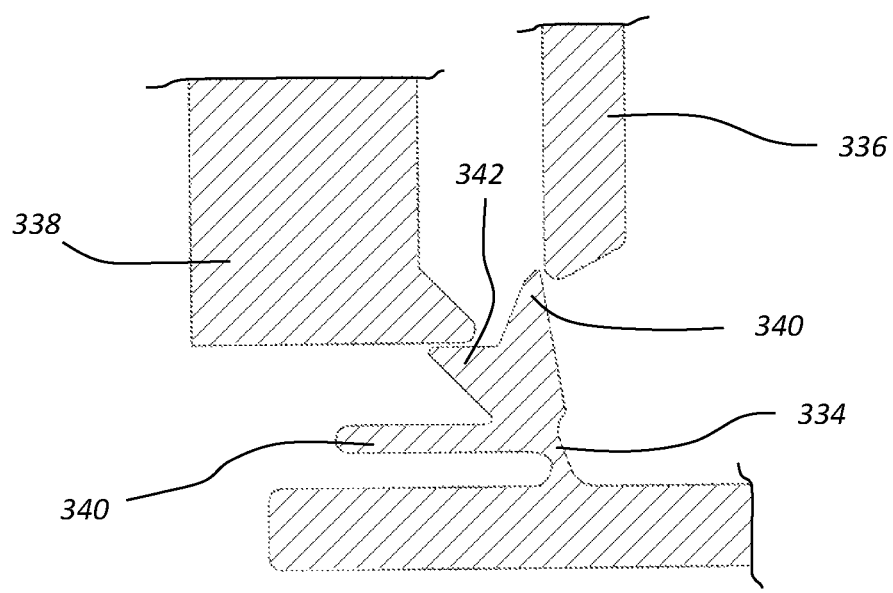

FIGS. 12 through 14 illustrate cross-sectional views taken along line 12-12 shown in FIG. 11. FIG. 12 illustrates the overhang 336 and hinge assembly 334 prior to initial attachment of the electronics package (i.e., while the hinge assembly 334 is in a receiving configuration). A portion of the outer rim of the electronics package defines a foot member 338. As shown in FIG. 13, as the electronics package is brought into contact with the patch assembly, the foot member 338 engages with a catch extension 340 of the hinge assembly 334. Further downward movement of the foot member 338 causes the hinge assembly 334 to pivot toward the foot member 338. As the hinge assembly 334 pivots, a tab 340 is forced from a position on a first side of the overhang 336 (the side opposite the foot member 338) to a position on a second side of the overhang 336 (the side coinciding with the foot member 338). This positions the hinge assembly 334 in a blocking configuration.

In the attached position shown in FIG. 13, the foot member 338 is positioned between the catch extension 340 and an angled stop 342. The angled stop 342 extends outwardly and upwardly to prevent inadvertent detachment of the foot member 338 from the hinge assembly 334. When detachment is desired, an appropriate amount of upward force can lift the foot member 338 past the angled stop 342. Additionally, or alternatively, the foot member can be moved away from the raised perimeter section (e.g., via a quick release button or other mechanical feature) to provide clearance from the angled stop 342 to facilitate removal.

As shown in FIG. 14, when a reattempt to attach the electronics package is made, the foot member 338 will butt against the outwardly oriented hinge assembly 334 before it can be fully pressed downward and attached to the inlay 314, making it difficult to attach the electronics package to an already used patch assembly.

Figure 15:
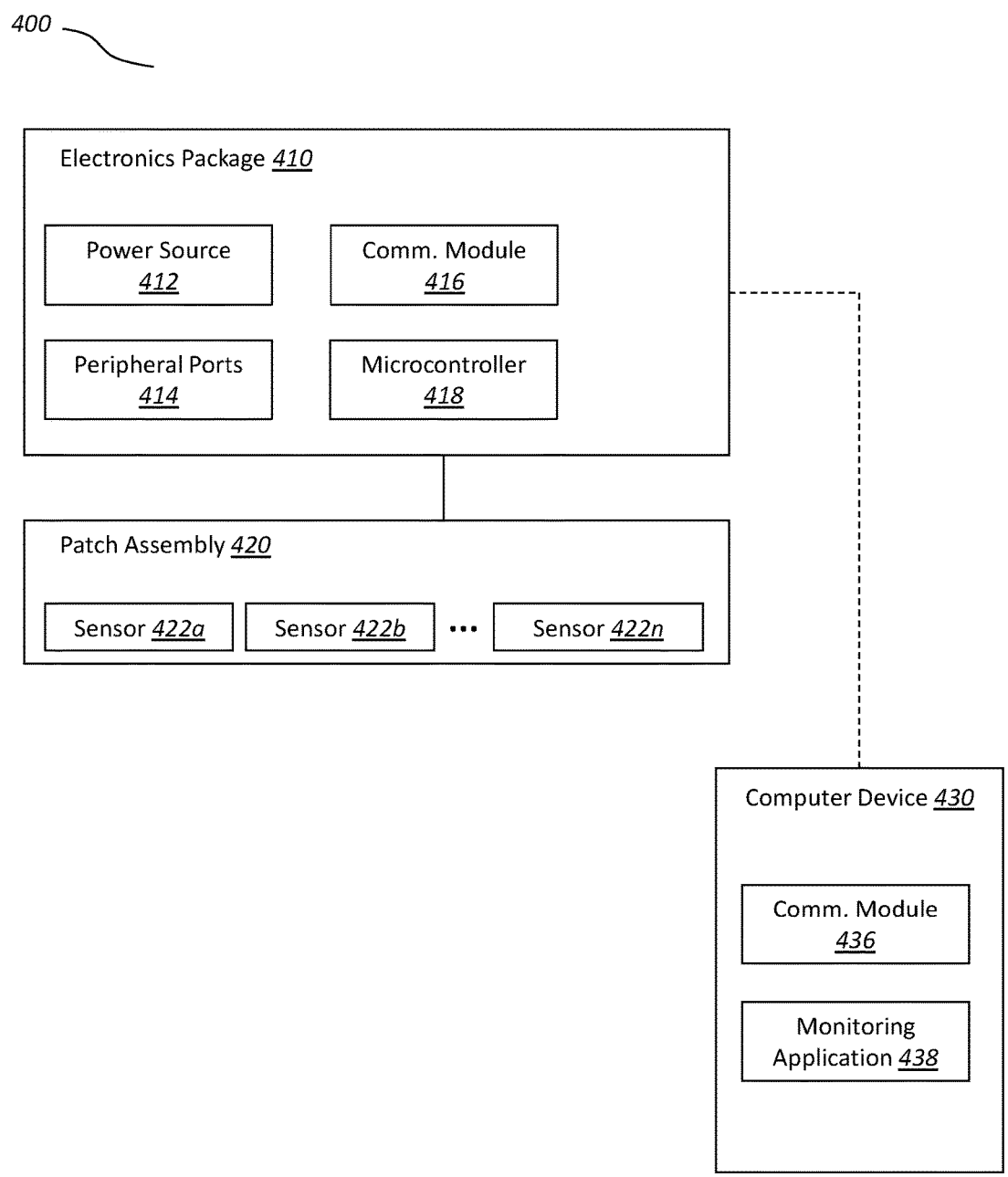
FIG. 15 illustrates an exemplary vital sign monitoring system including a vital sign monitoring device in communication with a computer device having a monitoring application.

In the illustrated embodiment, the foot member 338 of the electronics package is shown as being disposed on an outer side of the raised perimeter section 315 of the inlay 314. In alternative embodiments, the electronics package may attach with the foot member 338 being disposed on the inner side of the raised perimeter section 315. Thus, although the following description is directed to an outer side attachment of the electronics package, it will be understood that the same principles may be utilized for an inner side attachment of the electronics package. For an inner side attachment embodiment, the "outward" and "inward" references of the foregoing description are reversed, but the description is otherwise applicable FIG. 15 illustrates an exemplary vital sign monitoring system 400. In the illustrated embodiment, an electronics package 410 is coupled to a patch assembly 420. The electronics package 410 includes a power supply 412, such as a lithium-ion polymer battery or other suitable battery. The power supply 412 powers a microcontroller 418 and other components of the electronics package 410 and coupled patch assembly 420. Sensors within the patch assembly which require external power (e.g., a pulse oximetry sensor) are also powered by the power supply 412.

The illustrated electronics package 410 also includes one or more peripheral ports 414, which may be optionally utilized to communicatively link one or more other monitoring devices (e.g., blood pressure cuff, electrocardiogram equipment). The patch assembly 420 includes one or more embedded sensors 422a, 422b, 422n (referred to collectively as sensor(s) 422). A variety of different sensors may be utilized, as indicated by the ellipses.

The microcontroller 418 includes a processor and memory and is configured to receive sensor input from the patch assembly 420 and provide sufficient processing to enable sending of sensor readings to a display of the electronics package 410 and/or to a computer device 430. Other circuit components know in the art may also be utilized to provide desired functionality to the electronics package 410 (e.g., battery charging components, RAM components, regulators, analog front ends, and the like).

The illustrated electronics package 410 also includes a communication module 416, which enables received sensor readings to be communicated to one or more separate computer devices, such as illustrated computer device 430. The computer device 430 may be a mobile computer device (e.g., smart phone), personal computer, laptop, tablet, or other computer device. In the illustrated embodiment, the computer device includes a monitoring application 438, which may be utilized to receive sensor readings and any pre-processing done by the microcontroller 418. The monitoring application 438 may be configured to display vital sign readings, alerts, status indicators, battery levels, or other such information on a display of the computer device 430.

The electronics package 410 may be communicatively coupled to the computer device 430 (e.g., via communication modules 416 and 436) via a hardwired connection or via a wireless connection (e.g., Bluetooth).

Figure 16:
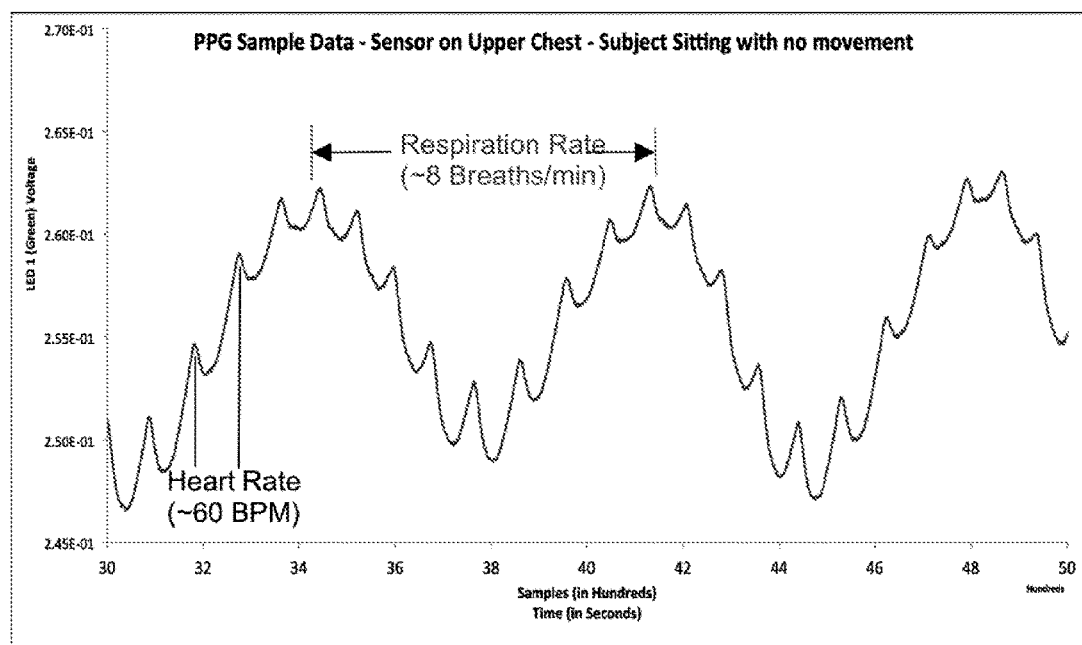
FIG. 16 illustrates a photoplethysmogram obtained using a vital sign monitoring device, the photoplethysmogram showing both measured heart rate and measured respiration rate.

FIG. 16 is a photoplethysmogram showing data obtained from a monitoring device with embedded pulse oximetry sensor configured according to the present disclosure. As shown, the device was able to provide effective monitoring of a subject's heart rate and respiration rate.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any of the single-use mechanisms described herein may be utilized with any of the electronics package embodiments and/or patch assembly embodiments described herein, and any element or component described in relation to a particular embodiment may be combined with or substituted for like components described in other embodiments.

The invention claimed is:

1. A vital sign monitoring device, comprising:
   a patch assembly, the patch assembly including:
      an adhesive layer having a lower side and an upper side, the adhesive layer being configured for application to a patient's skin;
      a vital sign sensor assembly embedded within the adhesive layer;
      a circuit member electrically coupled to the vital sign sensor assembly on the upper side of the adhesive layer; and
      an inlay having a raised perimeter section surrounding the circuit member and defining an interior space within the patch assembly; and
   an electronics package, the electronics package including:
      a fastener element configured to engage with the inlay to detachably couple the electronics package to the patch assembly;
      a power supply; and
      a microcontroller operatively coupled to the power supply and being disposed so as to be electrically coupled to the circuit member when the electronics package is coupled to the patch assembly.

2. The device of claim 1, wherein the vital sign sensor assembly is embedded within the adhesive layer and is configured to contact against the patient's skin when the adhesive layer is applied to the patien's skin.

3. The device of claim 1, wherein the vital sign sensor assembly includes one or more pulse oximetry sensors.

4. The device of claim 1, wherein the vital sign sensor assembly includes one or more body temperature sensors.

5. The device of claim 1, wherein the power supply and microcontroller are received within the interior space when the electronics package is coupled to the patch assembly.

6. The device of claim 1, wherein the circuit member is a flexible circuit member.

7. The device of claim 6, wherein the electronics package further comprises an electrical contact point electrically coupled to the microcontroller, the contact point being contacted to the flexible circuit member when the electronics package is coupled to the patch assembly.

8. The device of claim 1, wherein the adhesive layer includes a hydrogel component.

9. The device of claim 1, wherein the patch assembly further comprises a barrier layer disposed between the circuit member and the adhesive layer, the barrier layer being configured to reduce electrical noise transferred to the circuit member through the adhesive layer.

10. The device of claim 1, wherein the electronics package further comprises a communication module configured to transmit sensor readings to one or more communicatively linked computer devices.

11. The device of claim 1, wherein the patch assembly further comprises an overlay disposed upon the inlay to seal the inlay against underlying portions of the patch assembly.

12. The device of claim 1, further comprising a single-use attachment mechanism configured to limit operability of the patch assembly after an initial attachment and detachment.

13. The device of claim 12, wherein the electronics package includes a pointed element configured to contact and crimp the circuit member when the electronics package is initially coupled to the patch assembly, the crimped circuit member thereby bending out of alignment with an electrical contact point of the electronics package upon subsequent detachment of the electronics package from the patch assembly.

14. The device of claim 13, wherein the circuit member is disposed between the pointed element and at least a portion of the inlay, the inlay being shaped to receive the pointed element so that the circuit member is crimped between the inlay and the pointed element.

15. The device of claim 12, wherein the raised perimeter section of the inlay includes a hinge assembly configured to engage with the electronics package, the hinge assembly being configured to rotate from a receiving configuration to a blocking configuration when the electronics package is initially coupled to the patch assembly.

16. The device of claim 15, wherein the hinge assembly includes a living hinge.

17. A vital sign monitoring device, comprising:
a patch assembly, the patch assembly including:
an adhesive layer having a lower side and an upper side, the adhesive layer being configured for application to a patient's skin;
a vital sign sensor assembly embedded within the adhesive layer, the vital sign sensor assembly including one or more pulse oximetry sensors;
a flexible circuit member electrically coupled to the vital sign sensor assembly on the upper side of the adhesive layer; and
an inlay having a raised perimeter section surrounding the circuit member and defining an interior space within the patch assembly; and
an electronics package, the electronics package including:
a fastener element configured to engage with the inlay to detachably couple the electronics package to the patch assembly;
a power supply; and
a microcontroller operatively coupled to the power supply and being disposed so as to be electrically coupled to the circuit member when the electronics package is coupled to the patch assembly,
wherein the patch assembly and the electronics package are attachable by a single-use attachment mechanism configured to limit operability of the patch assembly after an initial attachment and detachment.

18. The device of claim 17, wherein the electronics package includes a pointed element configured to contact and crimp the circuit member when the electronics package is initially coupled to the patch assembly, the crimped circuit member thereby bending out of alignment with an electrical contact point of the electronics package upon subsequent detachment of the electronics package from the patch assembly.

19. The device of claim 17, wherein the raised perimeter section of the inlay includes a hinge assembly configured to engage with the electronics package, the hinge assembly being configured to rotate from a receiving configuration to a blocking configuration when the electronics package is initially coupled to the patch assembly.

20. A method of monitoring one or more patient vital signs, the method comprising:
providing a vital sign monitoring device, the vital sign monitoring device including a patch assembly coupled to an electronics package, the patch assembly including:
an adhesive layer having a lower side and an upper side, the adhesive layer being configured for application to a patient's skin;
a vital sign sensor assembly embedded within the adhesive layer;
a circuit member electrically coupled to the vital sign sensor assembly on the upper side of the adhesive layer; and
an inlay having a raised perimeter section surrounding the circuit member and defining an interior space within the patch assembly;
and the electronics package including:
a fastener element configured to engage with the inlay to detachably couple the electronics package to the patch assembly;
a power supply; and
a microcontroller operatively coupled to the power supply and being disposed so as to be electrically coupled to the circuit member when the electronics package is coupled to the patch assembly;
applying the vital sign monitoring device to a patient's skin; and
obtaining one or more vital sign measurements from the vital sign monitoring device.

* * * * *